(12) United States Patent
Roslin

(10) Patent No.: US 8,088,132 B2
(45) Date of Patent: Jan. 3, 2012

(54) ANASTOMOTIC OUTLET REVISION

(75) Inventor: Mitchell Roslin, Armonk, NY (US)

(73) Assignee: Davol, Inc. (a C.R. Bard Company), Warwick, RI (US)

( * ) Notice: Subject to any disclaimer, the term of this patent is extended or adjusted under 35 U.S.C. 154(b) by 1003 days.

(21) Appl. No.: 11/793,892

(22) PCT Filed: Dec. 16, 2005

(86) PCT No.: PCT/US2005/045724
§ 371 (c)(1),
(2), (4) Date: Dec. 5, 2007

(87) PCT Pub. No.: WO2006/068970
PCT Pub. Date: Jun. 29, 2006

(65) Prior Publication Data
US 2008/0161787 A1      Jul. 3, 2008

Related U.S. Application Data

(60) Provisional application No. 60/637,880, filed on Dec. 21, 2004.

(51) Int. Cl.
*A61B 17/08* (2006.01)
(52) U.S. Cl. ............................................. 606/153
(58) Field of Classification Search .............. 606/139, 606/144, 151, 153–155, 148; 623/23.65–23.68; 128/898; 514/1.2, 12.1, 21.1–21.3
See application file for complete search history.

(56) References Cited

U.S. PATENT DOCUMENTS

| 5,234,454 A | 8/1993 | Bangs |
| 5,322,697 A | 6/1994 | Meyer |

(Continued)

FOREIGN PATENT DOCUMENTS

| GB | 1174814 | 12/1969 |

(Continued)

OTHER PUBLICATIONS

Written Opinion of International Searching Authority.

*Primary Examiner* — Kevin T Truong
(74) *Attorney, Agent, or Firm* — Wolf, Greenfield & Sacks, P.C.

(57) ABSTRACT

A method is provided that involves endoscopically repairing or revising an anastomotic outlet previously formed in a portion of a patient's stomach as part of an earlier bariatric surgical procedure. The method may allow a surgeon to alter gastric functionality, such as gastric emptying or gastric dumping, by revising an existing anastomotic outlet. In this manner, the size of the outlet may be adjusted to change the rate at which contents pass from the stomach through the outlet. A surgical device may be inserted transorally through the patient's mouth, down through the esophagus and into the stomach or gastric pouch where it may be positioned in the vicinity of the anastomotic outlet. The surgical device may then be employed to revise the outlet to achieve a desired outlet configuration. The anastomotic outlet may be revised using an endoscopic fastening device that is configured to place a fastener in tissue. The fastening device may include an endoscopic suturing device to place one or more sutures in tissue in the region of the anastomotic outlet. One or more plications may be formed in the region of the outlet to narrow or reduce the opening of the anastomotic outlet.

31 Claims, 4 Drawing Sheets

U.S. PATENT DOCUMENTS

| | | |
|---|---|---|
| 5,355,897 A | 10/1994 | Pietrafitta et al. |
| 5,423,872 A | 6/1995 | Cigaina |
| 5,820,584 A | 10/1998 | Crabb |
| 6,044,846 A | 4/2000 | Edwards |
| 6,097,984 A | 8/2000 | Douglas |
| 6,234,955 B1 | 5/2001 | Silverman et al. |
| 6,238,335 B1 | 5/2001 | Silverman et al. |
| 6,248,058 B1 | 6/2001 | Silverman et al. |
| 6,251,063 B1 | 6/2001 | Silverman et al. |
| 6,251,064 B1 | 6/2001 | Silverman et al. |
| 6,405,732 B1 | 6/2002 | Edwards et al. |
| 6,530,878 B2 | 3/2003 | Silverman et al. |
| 6,533,717 B2 | 3/2003 | Silverman et al. |
| 6,540,789 B1 | 4/2003 | Silverman et al. |
| 6,558,400 B2 | 5/2003 | Deem |
| 6,562,034 B2 | 5/2003 | Edwards et al. |
| 6,572,627 B2 | 6/2003 | Gabbay |
| 6,572,629 B2 | 6/2003 | Kalloo |
| 6,575,896 B2 | 6/2003 | Silverman et al. |
| 6,589,238 B2 | 7/2003 | Edwards et al. |
| 6,591,838 B2 | 7/2003 | Durgin |
| 6,595,903 B2 | 7/2003 | Silverman et al. |
| 6,595,910 B2 | 7/2003 | Silverman et al. |
| 6,600,953 B2 | 7/2003 | Flesler et al. |
| 6,605,294 B2 | 8/2003 | Sawhney |
| 6,613,047 B2 | 9/2003 | Edwards |
| 6,675,809 B2 | 1/2004 | Stack et al. |
| 6,712,814 B2 | 3/2004 | Edwards et al. |
| 6,736,828 B1 | 5/2004 | Adams et al. |
| 6,740,082 B2 | 5/2004 | Shadduck |
| 6,740,121 B2 | 5/2004 | Geitz |
| 6,802,841 B2 | 10/2004 | Utley et al. |
| 6,802,868 B2 | 10/2004 | Silverman et al. |
| 6,846,312 B2 | 1/2005 | Edwards et al. |
| 6,866,663 B2 | 3/2005 | Edwards et al. |
| 6,901,295 B2 | 5/2005 | Sharma |
| 6,916,332 B2 | 7/2005 | Adams |
| 6,981,978 B2 | 1/2006 | Gannoe |
| 6,986,737 B2 | 1/2006 | Suzuki et al. |
| 7,037,315 B2 | 5/2006 | Sancoff et al. |
| 7,037,343 B2 | 5/2006 | Imran |
| 7,152,607 B2 | 12/2006 | Stack et al. |
| 7,175,638 B2 | 2/2007 | Gannoe et al. |
| 7,175,669 B2 | 2/2007 | Geitz |
| 7,201,757 B2 | 4/2007 | Knudson et al. |
| 7,220,284 B2 | 5/2007 | Kagan et al. |
| 7,238,191 B2 | 7/2007 | Bachmann |
| 7,239,912 B2 | 7/2007 | Dobak |
| 7,316,716 B2 * | 1/2008 | Egan .......................... 623/23.65 |
| 7,431,725 B2 * | 10/2008 | Stack et al. .................... 606/151 |
| 7,666,195 B2 * | 2/2010 | Kelleher et al. ................ 606/139 |
| 2002/0055757 A1 | 5/2002 | Torre et al. |
| 2002/0082621 A1 | 6/2002 | Schurr et al. |
| 2002/0107530 A1 | 8/2002 | Sauer |
| 2002/0139379 A1 | 10/2002 | Edwards et al. |
| 2002/0161414 A1 | 10/2002 | Flesler et al. |
| 2002/0183768 A1 | 12/2002 | Deem et al. |
| 2002/0188354 A1 | 12/2002 | Peghini |
| 2003/0014086 A1 | 1/2003 | Sharma |
| 2003/0024538 A1 | 2/2003 | Edwards et al. |
| 2003/0078466 A1 | 4/2003 | Silverman |
| 2003/0120321 A1 | 6/2003 | Bumm |
| 2003/0135206 A1 | 7/2003 | Edwards et al. |
| 2003/0144708 A1 | 7/2003 | Starkebaum |
| 2003/0158601 A1 | 8/2003 | Silverman et al. |
| 2003/0161887 A1 | 8/2003 | Klein |
| 2003/0181958 A1 | 9/2003 | Dobak, III |
| 2003/0188755 A1 | 10/2003 | Milbocker |
| 2003/0195509 A1 | 10/2003 | Edwards et al. |
| 2003/0208209 A1 | 11/2003 | Gambale |
| 2003/0220660 A1 | 11/2003 | Kortenbach et al. |
| 2003/0233108 A1 | 12/2003 | Gellman |
| 2003/0236536 A1 | 12/2003 | Grigoryants et al. |
| 2004/0006351 A1 | 1/2004 | Gannoe |
| 2004/0009224 A1 | 1/2004 | Miller |
| 2004/0015201 A1 | 1/2004 | Greenstein |
| 2004/0019388 A1 | 1/2004 | Starkebaum |
| 2004/0030217 A1 | 2/2004 | Yeung |
| 2004/0037865 A1 | 2/2004 | Miller |
| 2004/0044376 A1 | 3/2004 | Flesler et al. |
| 2004/0082859 A1 | 4/2004 | Schaer |
| 2004/0082950 A1 | 4/2004 | Edwards et al. |
| 2004/0082963 A1 | 4/2004 | Gannoe et al. |
| 2004/0087976 A1 | 5/2004 | DeVries et al. |
| 2004/0089313 A1 | 5/2004 | Utley et al. |
| 2004/0092892 A1 | 5/2004 | Kagan et al. |
| 2004/0096514 A1 | 5/2004 | Vogel et al. |
| 2004/0122470 A1 | 6/2004 | Deem et al. |
| 2004/0122526 A1 | 6/2004 | Imran |
| 2004/0133220 A1 | 7/2004 | Lashinski et al. |
| 2004/0138744 A1 | 7/2004 | Lashinski et al. |
| 2004/0147921 A1 | 7/2004 | Edwards et al. |
| 2004/0153146 A1 | 8/2004 | Lashinski |
| 2004/0162568 A1 | 8/2004 | Saadat |
| 2004/0186502 A1 | 9/2004 | Sampson |
| 2004/0204708 A1 | 10/2004 | Edwards et al. |
| 2004/0215180 A1 | 10/2004 | Starkebaum |
| 2004/0248188 A1 | 12/2004 | Sanders |
| 2004/0260316 A1 | 12/2004 | Knudson et al. |
| 2005/0024222 A1 | 2/2005 | Nelson |
| 2005/0033331 A1 | 2/2005 | Burnett et al. |
| 2005/0033332 A1 | 2/2005 | Burnett |
| 2005/0055038 A1 | 3/2005 | Kelleher |
| 2005/0055039 A1 | 3/2005 | Burnett et al. |
| 2005/0060030 A1 | 3/2005 | Lashinski et al. |
| 2005/0085829 A1 | 4/2005 | Kraemer et al. |
| 2005/0085923 A1 | 4/2005 | Levine et al. |
| 2005/0090873 A1 | 4/2005 | Imran |
| 2005/0137643 A1 | 6/2005 | Mintchev |
| 2005/0149072 A1 | 7/2005 | DeVries |
| 2005/0149200 A1 | 7/2005 | Silverman et al. |
| 2005/0154405 A1 | 7/2005 | Kraemer et al. |
| 2005/0159743 A1 | 7/2005 | Edwards et al. |
| 2005/0192614 A1 | 9/2005 | Binmoeller |
| 2005/0222492 A1 | 10/2005 | Adams |
| 2005/0246037 A1 | 11/2005 | Starkebaum |
| 2005/0267499 A1 | 12/2005 | Stack et al. |
| 2006/0020278 A1 | 1/2006 | Burnett et al. |
| 2006/0264983 A1 | 11/2006 | Holsten et al. |
| 2006/0276812 A1 | 12/2006 | Hill et al. |
| 2006/0282087 A1 | 12/2006 | Binmoeller |
| 2007/0032702 A1 | 2/2007 | Ortiz |
| 2007/0032800 A1 | 2/2007 | Ortiz et al. |
| 2007/0129735 A1 | 6/2007 | Filipi et al. |
| 2007/0129738 A1 | 6/2007 | Kraemer et al. |
| 2007/0167963 A1 | 7/2007 | Deem et al. |

FOREIGN PATENT DOCUMENTS

| | | |
|---|---|---|
| WO | WO 01/26588 | 4/2001 |
| WO | WO 03/094785 | 11/2003 |
| WO | WO 2004/019765 A2 | 3/2004 |
| WO | WO 2004/075974 | 9/2004 |
| WO | WO 2005/011463 | 2/2005 |
| WO | WO 2005/011519 | 2/2005 |
| WO | WO 2005/020802 | 3/2005 |
| WO | WO 2007/019268 | 2/2007 |

* cited by examiner

ANASTOMOTIC OUTLET REVISION

RELATED APPLICATIONS

This application claims the benefit of U.S. Provisional Application No. 60/637,880, filed Dec. 21, 2004, and is related to Document Disclosure No. 531,435, entitled "Transoral Approach For Improving Results After Gastric Bypass", dated May 8, 2003, by Mitchell Roslin.

BACKGROUND OF THE INVENTION

1. Field of the Invention

The present invention generally relates to bariatric surgery, and more specifically, to a method for repairing or revising an anastomotic outlet surgically formed in a patient's stomach.

2. Description of Related Art

Bariatric surgical procedures are available for treating various bariatric conditions. In some instances, an anastomotic outlet is surgically formed in a portion of the stomach as part of the bariatric procedure. For example, a gastric bypass procedure may involve the surgical formation of an anastomotic outlet where a segment of a patient's intestine is attached to bypass a portion of a patient's stomach and/or intestine.

Gastric bypass surgery has shown to be effective in the treatment of obesity by helping to reduce the amount of food eaten by the patient and the amount of calories absorbed by the gastrointestinal tract of the patient. Examples of gastric bypass procedures may include Roux-En-Y gastric bypass (RNYGB), mini-gastric bypass (MGB) and biliopancreatic diversion (BPD).

In a RNYGB procedure, the stomach is surgically separated into a small upper pouch that remains connected to the esophageal inflow, and a lower portion that is functionally detached from the upper pouch but remains connected to the intestinal tract for purposes of secreting digestive juices. A portion of the small intestine (jejunum) is anastomosed to the upper pouch, by performing a gastrojejunostomy (GJ), to bypass the lower portion of the stomach and the duodenum. The small upper pouch limits the amount of food eaten by a patient by creating a feeling of fullness upon the consumption of a relatively small amount of food.

RNYGB has proven effective in achieving short-term weight loss. However, a patient may experience post gastric bypass recidivism, whereby the patient may relapse and regain weight after a period of time following the bypass procedure. Several factors believed to contribute to recidivism include widening of the gastrojejunostomy, enlargement of the gastric pouch, increased accommodation of the gastric pouch, increased emptying of the gastric pouch and subconscious behavioral adaptation that allows a patient to learn how to consume more food. Surgical options for treating recidivism include reducing the size of the gastric pouch, banding the gastric pouch, re-performing the GJ anastomosis, or relocating the bypass. Such revisions involve a major surgical procedure that may potentially carry significant risk.

SUMMARY OF THE INVENTION

In one illustrative embodiment of the invention, a gastric surgical method is provided. The method includes endoscopically revising an anastomotic outlet previously formed in a portion of a stomach of a patient as part of a gastric surgical procedure.

In another illustrative embodiment of the invention, a method is provided for treating obesity. The method includes endoscopically revising an anastomotic outlet previously formed in a stomach portion of a patient as part of a gastric bypass procedure.

BRIEF DESCRIPTION OF THE DRAWINGS

Various embodiments of the invention will now be described, by way of example, with reference to the accompanying drawings, in which.

DETAILED DESCRIPTION

Figure 1:
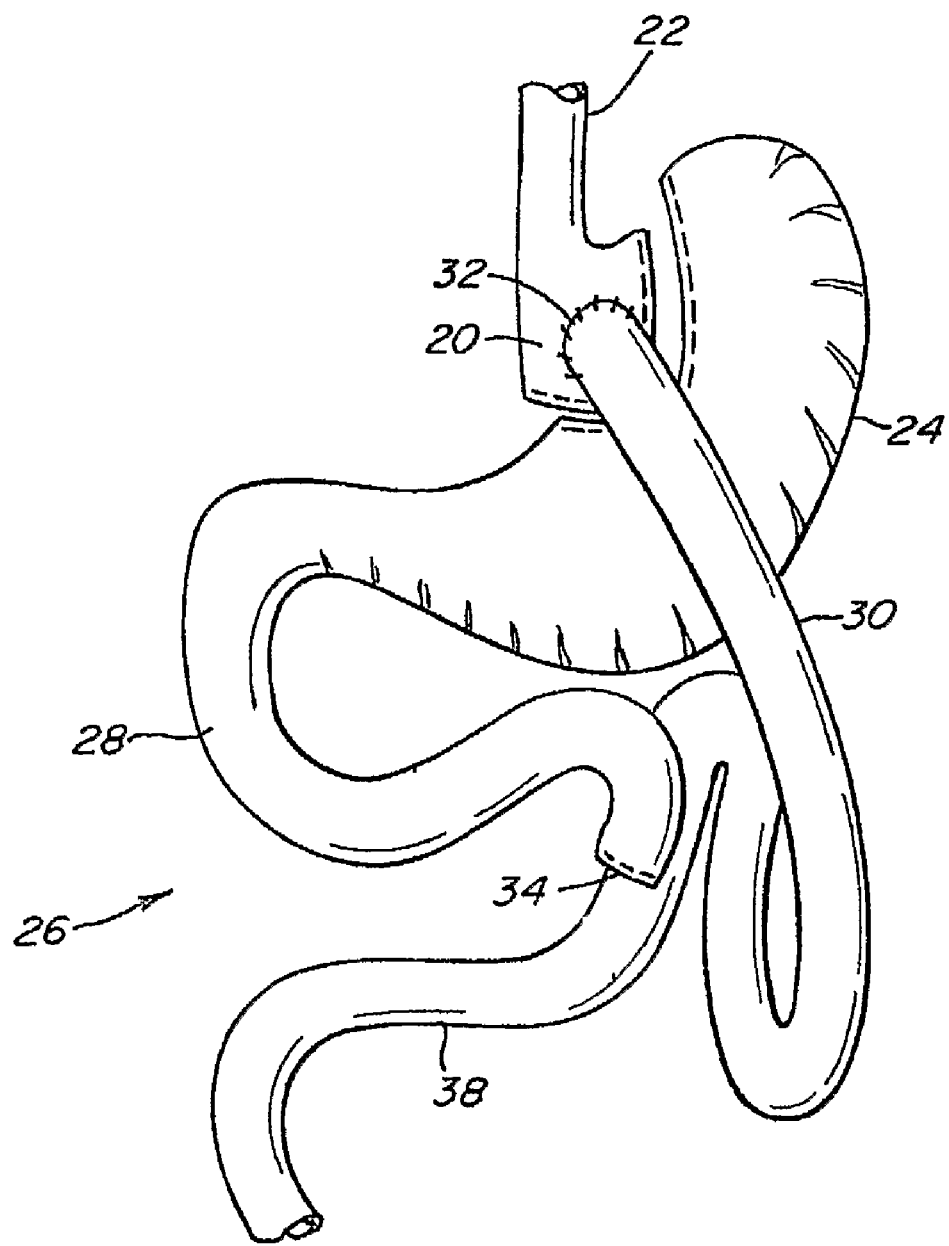
FIG. 1 is a schematic view of a portion of a gastrointestinal tract that has been modified by a Roux-En-Y gastric bypass procedure.

The invention is directed to a gastric surgical method that involves the repair or revision of an anastomotic outlet previously formed in a portion of a patient's stomach as part of an earlier bariatric surgical procedure. More particularly, the method may allow a surgeon to alter gastric functionality, such as gastric emptying or gastric dumping, by revising an existing anastomotic outlet. In this manner, the size of the outlet may be adjusted to change the rate at which contents pass from the stomach through the outlet.

For ease of understanding, and without limiting the scope of the invention, the gastric surgical method is described below particularly in connection with revising an anastomotic outlet created in a human patient's stomach as part of a Roux-En-Y gastric bypass procedure (RNYGB). However, it is to be appreciated that the gastric surgical method of the invention may be employed to revise an anastomotic outlet created as part of other gastric surgical procedures, including other gastric bypass procedures, as would be apparent to one of skill in the art.

The anastomotic outlet formed during the RNYGB restricts the passage of food from the gastric pouch to the lower portion of the small intestine or jejunum. However, over a period of time following the bypass surgery, the anastomotic outlet may become stretched, enlarged and/or otherwise loosened, resulting in an increased rate of food passage out of the gastric pouch. This increased rate of gastric emptying from the pouch may then lead to an increased amount of food consumption by the patient and consequent weight gain or recidivism.

The gastric surgical method involves endoscopically revising a previously formed anastomotic outlet following the prior bariatric procedure, such as a gastric bypass. A surgical device may be inserted transorally through the patient's mouth, down through the esophagus and into the gastric pouch where it may be positioned in the vicinity of the anastomotic outlet. The surgical device may then be employed to revise the outlet to achieve a desired outlet configuration. Advantageously, the procedure can be performed entirely from within the patient's stomach, obviating the need for a prolonged procedure, external incisions and, in some cases, general anesthesia.

The method may involve reducing the anastomotic outlet to a size that is sufficient to decrease the rate of food passage from the gastric pouch. In this manner, the smaller outlet will maintain food within the gastric pouch for a longer period of time and achieve a feeling of fullness with a relatively small amount of food intake, thereby lowering food consumption by the patient.

In one embodiment, the anastomotic outlet may be revised using an endoscopic fastening device that is configured to place a fastener in tissue. One or more fasteners may be placed in tissue in the region of the anastomotic outlet to form one or more tissue plications that narrow the opening or lumen of the anastomotic outlet so as to retard passage of the stomach contents and slow gastric emptying. It is to be understood that the invention is not limited to fastening tissue to narrow the outlet and that the outlet may be revised using any suitable technique apparent to one of skill in the art.

The fastening device may include an endoscopic suturing device to place one or more stitches in tissue in the region of the anastomotic outlet. The stitches may be tightened to form a revised outlet having a desired size or configuration for restricting passage of food from the gastric pouch. Suturing the tissue provides a predictable and reversible procedure with minimal risk of injury to areas remote from the target region of the procedure. However, it is to be understood that the surgical method is not limited to suturing tissue and that any suitable fastening device and fastener may be used to revise the outlet as would be apparent to one of skill in the art. For example, the tissue may be fastened with staples or clips, including shape-memory fasteners.

Alternatively or in addition to fastening tissue, other suitable endoscopic techniques apparent to one of skill in the art may be employed to narrow and/or tighten the anastomotic outlet. Such procedures may include bulking and/or scarring tissue in the vicinity of the anastomotic outlet. In one embodiment, a bulking material may be injected into tissue to reduce the size of the outlet opening. In another embodiment, energy may be applied to tissue which causes tissue damage that promotes a fibrotic response and leads to tissue healing which narrows the outlet.

Figure 2:
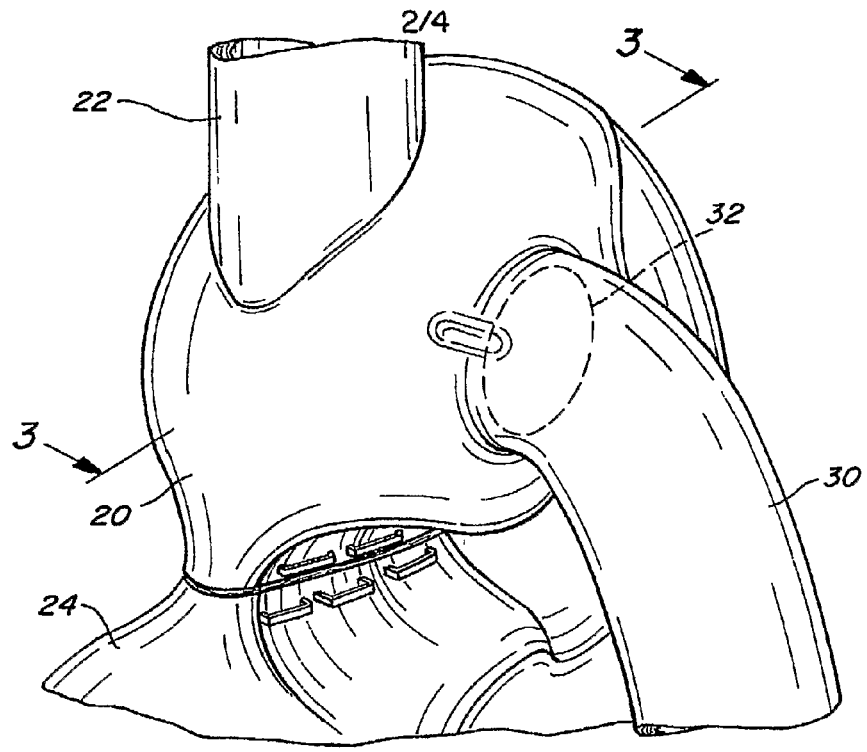
FIG. 2 is an enlarged isometric view of the modified stomach of FIG. 1 illustrating the gastric pouch and the connection between the jejunum and the gastric pouch to form a gastric bypass.

As illustrated in FIGS. 1-2, a Roux-En-Y gastric bypass involves surgically creating a small gastric pouch 20 which is functionally separated from the lower or distal portion 24 of the stomach. The gastric pouch remains connected to the esophageal tract 22. The small intestine 26 is divided into a proximal segment 28 and a distal segment 30. The upper end of the distal segment 30 is anastomosed to the gastric pouch 20 at an anastomotic outlet 32 to form the Roux limb through which food flows from the gastric pouch, bypassing the lower portion 24 of the stomach and the proximal segment 28 of the intestine. The proximal segment 28, which forms the biliopancreatic branch, is reattached to a portion 34 of the small intestine to permit the flow of digestive secretions from the lower portion of the stomach. A common channel 38, where food is mixed with digestive juices, is located distal to the Roux limb and the biliopancreatic branch below the connection between the biliopancreatic branch and the intestine.

After some period of time following the gastric bypass surgery, a patient may experience post gastric bypass recidivism, whereby the patient may relapse and regain weight. If recidivism occurs, it may be desirable to revise the surgically formed anastomotic outlet to establish or reestablish a gastric restriction that is sufficient to reduce the rate of emptying from the gastric pouch.

In one illustrative embodiment shown in FIGS. 3a-3d, a flexible endoscope 40 is advanced transorally through the lumen of a patient's esophagus 22 into the gastric pouch 20 previously formed during the gastric bypass. A suturing device 42, attached to the tip of the endoscope, is advanced and positioned at the opening of the anastomotic outlet 32.

One or more stitches 44 may be placed in tissue at the junction of the jejunum 30 and the gastric pouch 20. The stitches may be placed at any desired locations relative to the anastomotic outlet 32 that are suitable to reduce the overall size of the outlet. For example, the stitches may be placed within, in front of or behind the anastomosis to draw tissue within the lumen and reduce the overall diameter of the outlet. Suturing the tissue may also increase the stiffness of the outlet requiring an increased force to pass food through the outlet into the jejunum.

Figure 3A:
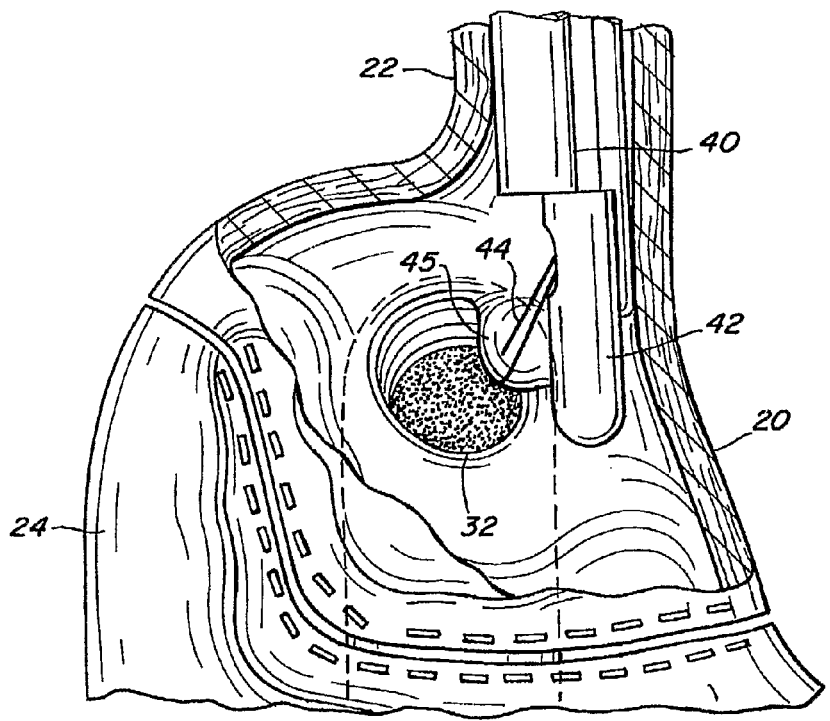
FIG. 3a is a partial fragmented view of the modified stomach taken along view line 3-3 of FIG. 2 illustrating a tissue bite taken at the anastomotic outlet with an endoscopic suturing device according to an illustrative embodiment of the invention.

As illustrated in FIG. 3a, a tissue bite is made at a first location adjacent the anastomotic outlet with a stitch 44 that is placed in the tissue using the suturing device. When tightened, the stitch may form a raised tissue portion or tissue protrusion 45 that can be effective in creating a restriction through the anastomotic outlet. In this regard, the raised tissue may reduce the size of anastomotic outlet opening. The stitched tissue may also tighten and increase the stiffness of the anastomotic outlet in a manner that restricts passage of food through the outlet.

Figure 3B:
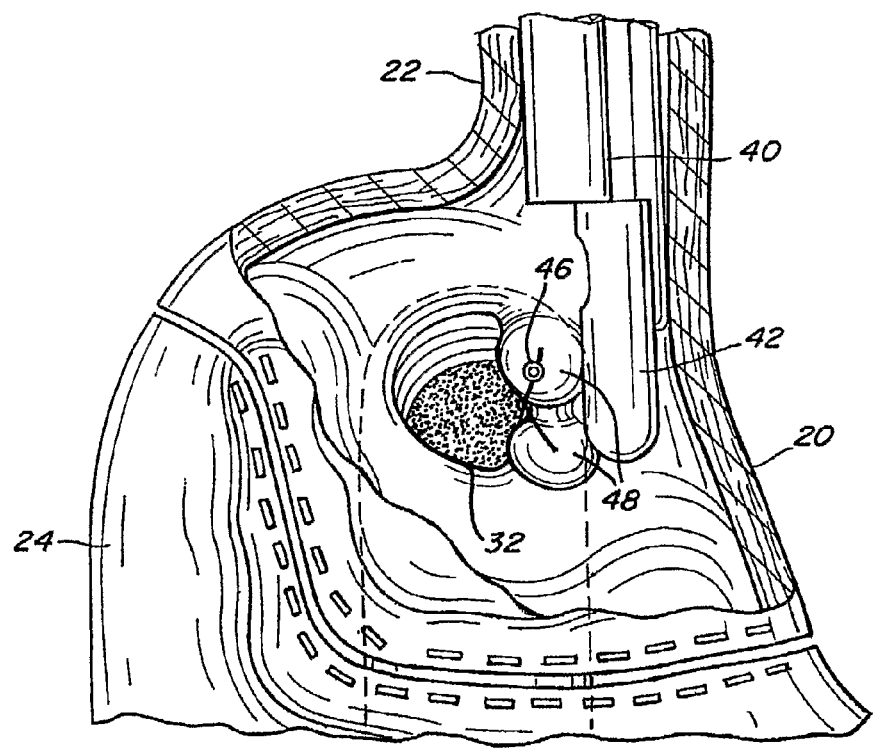
FIG. 3b is the partial fragmented view of FIG. 3a illustrating a pair of tissue bites cinched together with a suture to form a tissue plication at the anastomotic outlet.
Figure 3C:
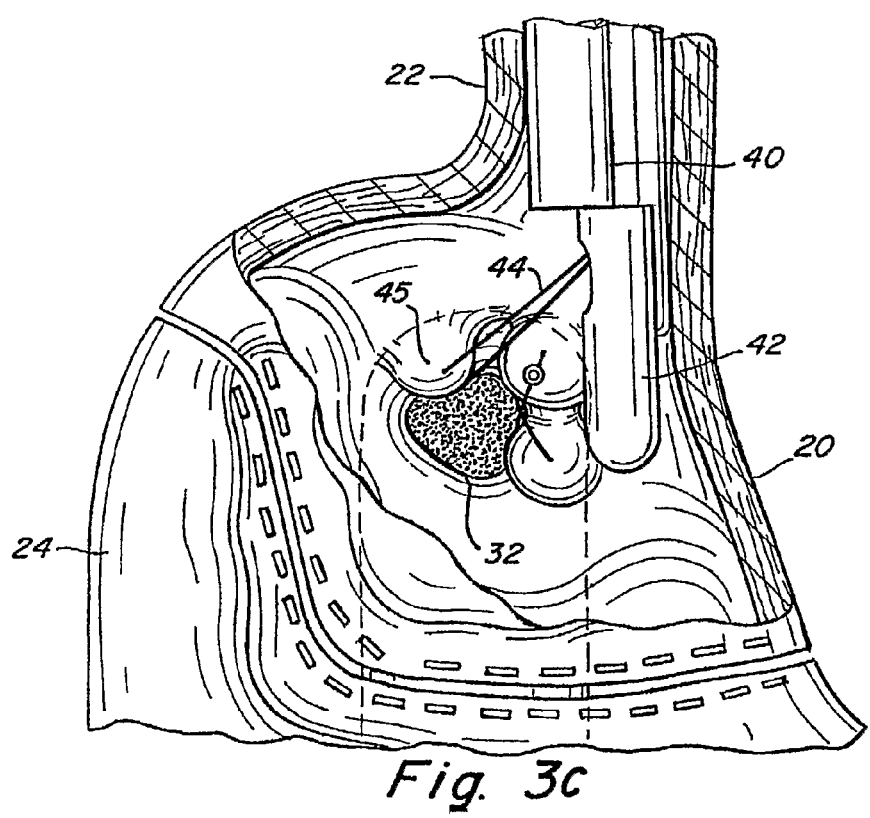
FIG. 3c is the partial fragmented view of FIG. 3b illustrating another tissue bite adjacent the tissue plication at the anastomotic outlet.
Figure 3D:
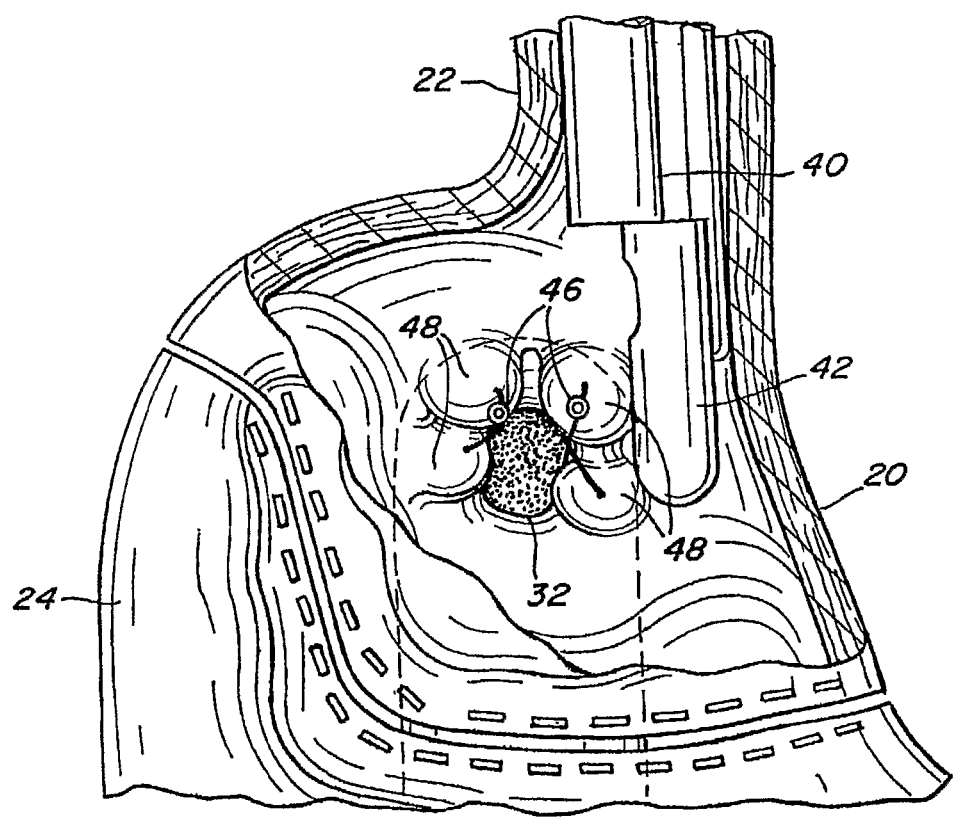
FIG. 3d is the partial fragmented view of FIG. 3c illustrating a second pair of tissue bites cinched together with a suture to form a second tissue plication at the anastomotic outlet.

As illustrated in FIG. 3b, a pair of tissue bites can be drawn together using a suture 44 that is fastened with a knot or clip 46 to form a plication or pleat 48 of tissue, preventing the tissue from returning to its original configuration. As illustrated in FIGS. 3c-3d, additional tissue bites may be taken and tightened at other desired locations to further reduce the outlet. In this regard, additional tissue plications 48 may be formed in the vicinity of the anastomosis to further reduce the outlet diameter. Although multiple sutures may be employed to revise the anastomotic outlet, it is to be appreciated that a single suture can be used to continuously stitch around the circumference of the anastomotic outlet. The sutures may be made of non-absorbable or absorbable material, as desired.

During a RNYGB procedure, the anastomotic outlet may be surgically formed with a diameter of about 1.1 centimeters (cm) to about 1.4 centimeters (cm) to provide a desired amount of restriction between the gastric pouch and the jejunum for regulating the rate of emptying from the gastric pouch. If the outlet becomes enlarged or dilated following the bypass procedure, the anastomotic outlet may be endoscopically revised to return the outlet diameter close to its original size to restrict outflow from the gastric pouch and induce weight loss in the patient. Additionally, even if the outlet has not become enlarged or dilated following the bypass surgery, it may be desirable to reduce the size of the anastomotic outlet to increase the restriction between the gastric pouch and the jejunum to induce further weight loss.

In one embodiment, the anastomotic outlet is revised to have a diameter of about 0.7 cm to about 2.0 cm. In another embodiment, the anastomotic outlet is revised to have a diameter of about 0.7 cm to about 1.5 cm. In a further embodiment, the anastomotic outlet is revised to have a diameter of about 1.0 cm to about 1.5 cm. In another embodiment, the anastomotic outlet is revised to have a diameter of about 0.7 cm to about 1.0 cm to allow for tissue swelling that may occur due to the suturing process. In a further embodiment, the anastomotic outlet is revised to have a diameter of about 1.5 cm to about 2.0 cm. It is to be understood that the outlet may be revised to have any suitable size apparent to one of skill in the art to achieve a desired level of restriction. In this regard, the outlet may be reduced to other sizes down to about 0.5 cm to achieve further restriction, if desired.

If it is determined that the anastomotic outlet is too restrictive, it may be enlarged using any suitable endoscopic procedure apparent to one of skill in the art. For example, the outlet may be enlarged using a balloon dilation procedure.

An endoscopic suturing device that may be particularly suited for the anastomotic outlet revision procedure is the EndoCinch™ suturing system available from C. R. Bard. The device is configured to draw tissue into a chamber using a vacuum after which a suture is placed through the tissue using a needle. One or more stitches may be placed at multiple locations using the device. It is to be appreciated, however, that any suitable fastening device, including other suturing devices, apparent to one of skill in the art may be employed to endoscopically revise the anastomotic outlet. For example, other tissue fastening techniques for mechanically reducing the size of the anastomotic outlet may include stapling or clipping tissue.

While the foregoing embodiment is directed to endoluminal suturing, it is to be appreciated that any suitable method of stiffening and/or reducing the size of the anastomotic outlet may be employed as would be apparent to one of skill in the art. For example, other methods for revising the outlet, in addition to or as an alternative to suturing, may include scarring or bulking techniques, or any combination thereof.

Scarring methods involve damaging tissue to promote a fibrotic response which leads to tissue healing that narrows and/or stiffens the outlet. Several illustrative embodiments of scarring techniques include, but are not limited to, tissue abrasion, tissue ablation, RF or ultrasound energy application, laser therapy, or sclerotherapy. In one embodiment, energy may be applied to the tissue to at least a depth of the submucosa. However, it is to be understood that the energy may be applied to any tissue layer apparent to one of skill in the art for promoting a desired fibrotic response. It is also to be appreciated that any suitable method apparent to one of skill in the art may be employed by which the formation of scar tissue is induced in the region of the anastomotic outlet.

Bulking methods involve injecting a material into tissue regions adjacent the anastomotic outlet to selectively increase the bulk of tissue in a manner that reduces the size of the outlet opening. Any suitable bulking method using any suitable bulking material apparent to one of skill in the art may be employed to bulk tissue in the region of the anastomotic outlet.

While the foregoing embodiments are directed to repairing or revising a surgically formed anastomotic outlet, it is also contemplated that this procedure may be used to repair or revise a gastric pouch or other portions of a stomach following bariatric surgery. In addition to post surgical repair or revision, it is further contemplated that this procedure may be used as a pre-surgical intervention to facilitate patient weight loss.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A gastric surgical method comprising an act of:
   (a) following a gastric surgical procedure, endoscopically revising an anastomotic outlet previously formed through a wall of a portion of a stomach of a patient as part of the gastric surgical procedure.

2. The gastric surgical method according to claim 1, further comprising act (b) of transorally inserting a surgical device into the patient.

3. The gastric surgical method according to claim 2, wherein the anastomotic outlet has an opening, and wherein act (a) includes adjusting the size of the anastomotic outlet opening.

4. The gastric surgical method according to claim 3, wherein act (a) includes adjusting the anastomotic outlet opening to have a diameter from 0.7 cm to 2.0 cm.

5. The gastric surgical method according to claim 4, wherein act (a) includes adjusting the diameter of the anastomotic outlet opening to be from 1.0 cm to 1.5 cm.

6. The gastric surgical method according to claim 3, wherein act (a) includes reducing the size of the anastomotic outlet opening.

7. The gastric surgical method according to claim 6, wherein act (a) includes fastening tissue at the anastomotic outlet to reduce the size of the anastomotic outlet opening.

8. The gastric surgical method according to claim 7, wherein the act of fastening includes suturing tissue at the anastomotic outlet.

9. The gastric surgical method according to claim 8, wherein act (b) includes inserting a suturing device into the patient.

10. The gastric surgical method according to claim 9, wherein act (a) includes forming at least one tissue plication.

11. The gastric surgical method according to claim 9, wherein act (a) includes capturing tissue with the suturing device.

12. The gastric surgical method according to claim 11, wherein the act of capturing includes applying a vacuum to the tissue.

13. The gastric surgical method according to claim 7, wherein act (a) includes applying energy to tissue at the anastomotic outlet to promote tissue scarring.

14. The gastric surgical method according to claim 6, wherein act (a) includes applying energy to tissue at the anastomotic outlet to promote tissue scarring.

15. The gastric surgical method according to claim 6, wherein act (a) includes injecting a bulking material into tissue at the anastomotic outlet.

16. A method of treating obesity comprising an act of:
   (a) following a gastric bypass procedure, endoscopically revising an anastomotic outlet previously formed through a wall of a stomach portion of a patient as part of the gastric bypass procedure.

17. The method according to claim 16, wherein the anastomotic outlet was created as part of a gastrojejunostomy performed during the gastric bypass procedure.

18. The method according to claim 17, wherein the gastric bypass procedure is a Roux-En-Y gastric bypass and the stomach portion is a gastric pouch separated from the remainder of the stomach.

19. The method according to claim 16, wherein the anastomotic outlet has an opening, and wherein act (a) includes adjusting the size of the anastomotic outlet opening.

20. The method according to claim 19, wherein act (a) includes adjusting the anastomotic outlet opening to have a diameter from 0.7 cm to 2.0 cm.

21. The method according to claim 20, wherein act (a) includes adjusting the diameter of the anastomotic outlet opening to be from 1.0 cm to 1.5 cm.

22. The method according to claim 19, wherein act (a) includes reducing the size of the anastomotic outlet opening.

23. The method according to claim 22, wherein act (a) includes fastening tissue at the anastomotic outlet to reduce the size of the anastomotic outlet opening.

24. The method according to claim 23, wherein the act of fastening tissue includes suturing tissue at the anastomotic outlet.

25. The method according to claim 24, further comprising act (b) of transorally inserting a suturing device into the patient.

26. The method according to claim 25, wherein act (a) includes forming at least one tissue plication.

27. The method according to claim 25, wherein act (a) includes capturing tissue with the suturing device.

28. The method according to claim 27, wherein the act of capturing includes applying a vacuum to the tissue.

29. The method according to claim 23, wherein act (a) includes applying energy to tissue at the anastomotic outlet to promote tissue scarring.

30. The method according to claim 16, wherein act (a) includes applying energy to tissue at the anastomotic outlet to promote tissue scarring.

31. The method according to claim 16, wherein act (a) includes injecting a bulking material into tissue at the anastomotic outlet.

* * * * *